US005518732A

United States Patent [19]

Nigam

[11] Patent Number: 5,518,732
[45] Date of Patent: May 21, 1996

[54] BIO-ERODIBLE OPHTHALMIC SHIELD

[75] Inventor: Alok Nigam, Trabuco Canyon, Calif.

[73] Assignee: Chiron Vision, Inc., Irvine, Calif.

[21] Appl. No.: 388,159

[22] Filed: Feb. 14, 1995

[51] Int. Cl.$^6$ ...................................................... A61F 2/14
[52] U.S. Cl. .................. 424/427; 514/954; 623/4
[58] Field of Search ........................ 424/427; 514/954; 623/4

[56] References Cited

U.S. PATENT DOCUMENTS

| | | | |
|---|---|---|---|
| 3,710,796 | 1/1973 | Neefe | 424/429 |
| 3,914,402 | 10/1975 | Shell | 424/428 |
| 3,960,150 | 6/1976 | Hussain et al. | 424/428 |
| 3,981,303 | 9/1976 | Higuchi et al. | 424/428 |
| 3,986,510 | 10/1976 | Higuchi et al. | 424/428 |
| 3,993,071 | 11/1976 | Higuchi et al. | 424/428 |
| 4,164,559 | 8/1979 | Miyata et al. | 424/428 |
| 4,223,984 | 9/1980 | Miyata et al. | 351/160 H |
| 4,233,360 | 11/1980 | Luck et al. | 424/443 |
| 4,264,155 | 4/1981 | Miyata | 351/160 H |
| 4,343,787 | 8/1982 | Katz | 424/428 |
| 4,505,855 | 3/1985 | Bruns et al. | 530/356 |
| 4,581,030 | 4/1986 | Bruns et al. | 623/5 |
| 4,600,533 | 7/1986 | Chu | 530/3576 |
| 4,865,846 | 9/1989 | Kaufman | 424/428 |
| 4,913,904 | 4/1990 | Fyodorov et al. | 424/427 |
| 4,946,450 | 8/1990 | Erwin | 604/294 |
| 5,036,056 | 7/1991 | Kludas | 514/54 |
| 5,053,388 | 10/1991 | Gibson et al. | 514/2 |
| 5,128,134 | 7/1992 | Fyodorov et al. | 424/427 |
| 5,137,728 | 8/1992 | Bawa | 424/427 |
| 5,156,839 | 10/1992 | Pennell et al. | 424/78.37 |
| 5,162,430 | 11/1992 | Rhee et al. | 525/54.1 |

(List continued on next page.)

FOREIGN PATENT DOCUMENTS 3904741   8/1989   Germany.

OTHER PUBLICATIONS

Aquavella, J. V. et al., *CLAO Journal*, vol. 14(1), 47–50 (1988).
Aquavella, J. V. et al., *J. Cataract Refract. Surg.*, vol. 14, 492–5 (1988).
Chen, Y. F. et al., *American Journal of Ophthamology*, vol. 109, 132–7 (1990).
"Corneal shields aid corneal healing process", article in *Ophthomology Times*.
Esswein, M. B. et al., Antimicrobial Efficacy of Antiseptic Containing Collagen Corneal Shields, Cullen Eye Institute, Baylor College of Medicine.
Frantz, J. M. et al., *American Journal of Ophthalmology*, vol. 108, 524–8 (1989).
Gussler, J. R. et al., *J. Cataract Refract. Surg.*, vol. 16, 719–22 (1990).
Hobden, J. A. et al., *Arch. Ophthalmol.*, vol. 106, 1605–7 (1988).
Hwang, D. G. et al., *Arch. Ophthalmol.*, vol. 107, 1375–80 (1989).

Kaufman, H., *J. Cataract Refract. Surg.*, vol. 14, 487–8 (1988).
Marmer, R. H., *J. Cataract Refract. Surg.*, vol. 14, 496–99 (1988).
Murray, T. G. et al., *Arch. Ophthamol.*, vol. 108, 104–6 (1990).
O'Brien, T. P. et al., *J. Cataract Refract. Surg.*, vol. 14, 505–7 (1988).
"Collagen shields for drug delivery to the cornea", *Ocular Therapy Report*, vol. 2(5), 17–20 (1989).
Phinney, R. B. et al., *Arch. Ophthalmol.*, vol. 106, 1599–1604 (1988).
Poland, D. E. et al., *J. Cataract Refract. Surg.*, vol. 14, 489–491 (1988).
Reidy, J. J. et al., *Ophthalmology*, vol. 97, 1201–3 (1990).
Reidy, J. J. et al., *Cornea*, vol. 9(3), 196–199 (1990).
Robin, J. B., "Collagen corneal shields", *Eye Facts*, UIC Eye Center, The University of Illinois at Chicago College of Medicine, Nov.–Dec 1988 issue.
Ruffini, J. J. et al., *Ophthalmic Surgery*, vol. 20, 21–25 (1989).
Sawusch, M. R. et al., *American Journal of Ophthalmology*, vol. 106, 279–281 (1988).
Sawusch, M. R. et al., *J. Cataract Refractive Surg.*, vol. 15, 625–8 (1989).
Schwartz, S. D. et al., *American J. of Ophthalmology*, vol. 109, 701–4 (1990).
Shofner, R. S. et al., *Ophthalmology Clinics of North America*, vol. 2, 15–23 (1989).
Unterman, S. R. et al., *J. Cataract Refract. Surg.*, vol. 14, 500–504 (1988).
Aquavella, J. V. et al., *Ophth. Surg.*, vol. 18(8), 570–3 (1987).
Boyd, B., Highlights of ophthalmology letter, vol. 17(2), 1–14 (1989).
Chvapil, M. et al., *Intl. Review of Conn. Tissue Research*, eds. Hall et al., vol. 6, 1–61 (1973).
Colin, J. et al., *J. Fr. Ophth.*, vol. 11(2), 137–41 (1988). In French: abstract in English.
Fourman, S. et al., *Am. J. Ophth.*, vol. 107(6), 673–4 (1989).
Groden, L. R. et al., *Arch. Ophth.*, vol. 104, 84–6 (1986).
Harrison, K. W., *J. of Ophth. Nurs. & Tech.*, vol. 8(3), 97–8 (1989).
Pillunat, L. E. et al., *Fortschr. Ophth.*, vol. 86, 192–4 (1989). In German; summary in English.
Prescott, L. M. et al., *Ophth. Times*, vol. 13(9), 4 (1988).
Shaker, G. J. et al., *CLAO Journal*, vol. 15(4), 298–304 (1989).
Wright, M., *Ophth. Times*, vol. 13(8), 6 & 19 (1988).

*Primary Examiner*—Carlos Azpuru
*Attorney, Agent, or Firm*—Rothwell, Figg, Ernst & Kurz

[57] ABSTRACT

Bio-erodible ophthalmic shields comprising gelatin, a glycosaminoglycan (for example chondroitin sulfate) and carboxymethyl cellulose, and a method of treating a traumatized or "dry" eye by administering the gelatin-based ophthalmic shields to the traumatized eye. The ophthalmic shields are bio-compatible and bio-erodible in traumatized, non-traumatized and dry eyes. The gelatin-based ophthalmic shields can further include one or more therapeutically active substances that will be released to the eye.

19 Claims, No Drawings

U.S. PATENT DOCUMENTS

| | | | |
|---|---|---|---|
| 5,185,152 | 2/1993 | Peyman | 424/427 |
| 5,188,826 | 2/1993 | Chandrasekaran et al. | 424/78.04 |
| 5,246,013 | 9/1993 | Frank et al. | 128/774 |
| 5,259,998 | 11/1993 | Reich et al. | 264/1.1 |
| 5,263,992 | 11/1993 | Guire | 623/66 |
| 5,264,214 | 11/1993 | Rhee et al. | 424/422 |
| 5,270,051 | 12/1993 | Harris | 424/427 |
| 5,304,169 | 4/1994 | Sand | 606/5 |
| 5,304,595 | 4/1994 | Rhee et al. | 525/54.1 |
| 5,306,500 | 4/1994 | Rhee et al. | 424/422 |
| 5,318,780 | 6/1994 | Viegas et al. | 424/427 |
| 5,324,775 | 6/1994 | Rhee et al. | 525/54.2 |
| 5,328,955 | 7/1994 | Rhee et al. | 525/54.1 |

BIO-ERODIBLE OPHTHALMIC SHIELD

BACKGROUND OF THE INVENTION

1. Technical Field

The present invention relates to bio-erodible ophthalmic shields and methods for their use, for example as a protective shield following eye surgery or other trauma to the eye. More specifically, the invention provides improved, gelatin-based bio-erodible ophthalmic shields that provide improved physical and therapeutic properties under a variety of physiological conditions of a traumatized or non-traumatized human eye.

2. Brief Description of the Background Art

The preparation of collagen-based ophthalmic shields ("collagen shields") and their use both with and without the incorporation of therapeutic agents (i.e., drugs for ocular administration) have been described in the literature. See, for example, Kaufman, "Collagen shield drug delivery: Therapeutic concentrations of tobramycin in the rabbit cornea and aqueous humor," *J. Cataract Refract. Surg.*, 14:500–504 (1988). Collagen of porcine or bovine origin often is employed, but, no matter what its source, the collagen first typically is solubilized by enzymatic treatment. The in vivo solubility or "bio-erodibility" of corneal shields prepared from enzyme-solubilized collagen is controlled by controlling the extent to which the collagen is cross-linked, either chemically or via the use of ultraviolet light. Inasmuch as native collagen is not soluble under normal physiologic conditions, control over the solubilization and cross-linking processes can be critical to the preparation of a final product having the desired dissolution rate. Unfortunately, variations in processing, raw material sources and other factors can make the wide-scale commercial production of such final products difficult.

Ophthalmic shields find one potential utility in the treatment of the traumatized (physically injured or post-surgery) eye by acting as a temporary protective bandage. Trauma, which may be caused for example by accidental injury or eye surgery, may be treated in part by the application of a corneal shield which serves to protect the tissue from irritation and infection, and fosters the growth of epithelial cells, thus providing increased patient comfort. Ideally, the ophthalmic shield could be comfortably worn for a period of several days while providing lubrication for the eye, physical protection from irritation and a favorable environment which fosters the healing process. Aquavella et al., "Therapeutic Applications of a Collagen Bandage Lens: A Preliminary Report," *The CLAO Journal*, 14:1 (1988) discusses the use of a "collagen bandage lens" following anterior segment surgery.

Not only can ophthalmic shields be used to protect the traumatized eye, but they also may be used to promote healing of the traumatized eye, thus decreasing the time required for healing. Poland et al., "Clinical Uses of Collagen Shields," *J Cataract Refract Surg*, 14:489–491 (1988) discusses clinical uses of collagen shields, including increased patient comfort, enhancement of epithelial healing, and drug delivery following surgery such as keratoplasty.

Ophthalmic shields also have been proposed for use as ocular drug delivery devices. The literature (Aquavella et al., "Use of Collagen Shields as a Surgical Adjunct," *J. Cataract Refract. Surg.*, 14:492–95 (1988)) contains reports of pilocarpine, tobramycin, gentamicin, dexamethasone and flurbiprofen being administered to the eye of a patient after being incorporated into a collagen-based ophthalmic shield. Collagen-based ophthalmic shields also can provide for the sustained delivery of a pharmaceutically active agent. The shield can be placed in the eye, such as in the inferior fornix or the inferior cul-de-sac, where it slowly dissolves under physiological conditions and slowly releases the drug.

Ophthalmic shields may also be used in the treatment of dry eye syndrome. The traditionally used artificial tear solutions have limited effectiveness because of their short retention time within the conjunctival sac. When long-acting, soluble, tear replacement preparations have been administered, ocular irritation and blurring of vision often resulted. In contrast, the literature reports that a collagen film inserted into the inferior cul-de-sac of normal patients dissolved over approximately seven hours and produced a prolonged tear film break-up time, without irritation or blurring. (Shaker et al., "Soluble Collagen Disks for the Treatment of Dry Eye Syndrome," *The CLAO Journal*, 15:4 (1989)). The collagen shields dissolve in the eye, becoming gel-like and eventually liquefying, thereby providing the "dry eye" with lubrication.

Excimer laser keratectomy has been widely described in the scientific literature and shows much promise for achieving commercial success as a surgical procedure for vision correction (e.g. correction of myopia) for human patients. Successful treatment of the eye that has been traumatized by the excimer laser keratectomy procedure, and successful wound healing in the eye, are important aspect of the total surgical care of the patient. This aspect of patient care is expected to be an important aspect of commercial success enjoyed by that surgical procedure.

The literature describes the use of collagen-based ophthalmic shields for, for example, ocular drug delivery and wound healing applications. See Shofner et al., "New Horizons in Ocular Drug Delivery," *Ophthalmology Clinics of North America*, 2:15–23 (1989); Aquavella et al., "Therapeutic Applications of a Collagen Bandage Lens: A Preliminary Report," *The CLAO Journal*, 14:1 (1988); Marmer, R., "Therapeutic and protective Properties of the Corneal Collagen Shield," *J Cataract Refract Surg.*, 14:496–499 (1988); Poland et al., "Clinical Uses of Collagen Shields," *J Cataract Refract Surg*, 14:489–491 (1988). However, due to the triple helix structure of collagen, collagen often exhibits unacceptable dissolution properties. Moreover, collagen ophthalmic shields can suffer from poor optical clarity. Therefore, a need exists for an ophthalmic shield with the properties of improved optical clarity and improved dissolution in traumatized, non-traumatized and "dry" eyes.

Additionally, the improved ophthalmic shield must exhibit good physical properties, especially optical clarity and bio-erodibility, in the environments of traumatized, non-traumatized and dry eyes. The physical, chemical and enzymatic characteristics of the normal eye differ from that of the traumatized eye following, for example, accidental injury or surgery. Normal human eyes exhibit a relatively constant tear rate, having a chemical and enzymatic composition that has been described in the literature. Lysozyme, an enzyme that hydrolyses the muramic acid linkages in the peptidoglycan of bacterial cell walls, is prevalent in the tears of the normal human eye. This enzyme plays an important bacteriocidal role in the tears. In the traumatized eye, however, tearing often is greatly increased, thereby diluting the normal complement of lysozyme and rendering the already-compromised eye susceptible to bacterial infections. The traumatized eye also exhibits elevated levels of a number of proteolytic enzymes, such as the collagenases. It has been found, for example, that enzyme levels can be very high following excimer laser eye surgery (photorefractive keratectomy). The condition known as dry eye, in contrast, is characterized by the presence of elevated levels of plasminogen. Collagen shields currently available tend to behave differently in the chemically—and enzymatically-different environments of the dry eye, the non-traumatized eye and the traumatized eye. Thus, a need has existed for an improved ophthalmic shield that would exhibit good physical properties, especially optical clarity, comfort and bio-erodibility characteristics, in these various conditions in the human eye.

SUMMARY OF THE INVENTION

Improved bio-erodible ophthalmic shields are provided according to one aspect of the present invention. The ophthalmic shields are composed of gelatin, a glycosaminoglycan such as chondroitin sulfate and carboxymethyl cellulose. According to a preferred aspect of the invention, gelatin, glycosaminoglycan and carboxymethyl cellulose are present as a (partially) crosslinked matrix, with the degree of crosslinking having been selected so as to provide desired physical properties of the final product. Gelatin typically provides the major (by weight) structural component, and the combination of ingredients provides the unique structural and functional characteristics of the corneal shield. The ability to pre-select a desired bio-erodibility (dissolution) rate, and the provision of in situ enzyme-deactivating functions, are included in these unique characteristics.

The gelatin-based ophthalmic shields of the present invention provide improved properties over the prior art collagen-based ophthalmic shields, these properties often including but not limited to improved optical clarity, improved comfort and/or improved dissolution ("bio-erodibility") characteristics. Specifically, the matrix of cross-linked gelatin, glycosaminoglycan and carboxymethyl cellulose provides an ophthalmic shield that is biocompatible and bio-erodible in traumatized, non-traumatized and dry eyes. Moreover, gelatin itself provides additional advantages over collagen, including cost, ease of use and freedom from adverse antigenic properties.

In other preferred aspects of the invention, the gelatin-based ophthalmic shields can further include one or more therapeutically active substances (e.g. pharmaceutical agents) that will be released to the eye. Therapeutically active substances can be easily incorporated into the inventive shields during rehydration of the shields immediately prior to use, or during the manufacturing process.

in yet another aspect of the invention, a method of promoting the healing of the eye comprises applying to a traumatized eye a gelatin-based ophthalmic shield according to the present invention. The trauma may be caused by, for example, accidental physical injury to the eye, eye surgery (including various forms of keratoplasty, keratotomy and keratectomy) or various diseases/conditions of the eye. Application of the ophthalmic shield following excimer laser surgery or as part of a treatment regimen for dry eye are particularly preferred applications of the inventive gelatin shield. The inventive gelatin shield provides special advantages over known collagen ophthalmic shields in these preferred applications.

Due to the proteolytic enzyme de-activating properties of the inventive corneal shield, the present invention also provides a method of reducing proteolytic damage to a traumatized eye by applying to the traumatized eye of a patient a shield according to the present invention.

DETAILED DESCRIPTION OF THE PREFERRED EMBODIMENTS

The present invention provides an improved, bio-erodible ophthalmic shield that can be placed upon a traumatized, non-traumatized or dry eye of a patient. The shield is composed of gelatin as the major structural component, a glycosaminoglycan and carboxymethyl cellulose. This unique combination of ingredients (which in the preferred embodiment are crosslinked together to provide a matrix of those components) provides a product that exhibits excellent optical clarity, biocompatibility and bio-erodibility characteristics in both the traumatized and non-traumatized eye of a human patient, as well as in a patient suffering from dry eye. The gelatin shield advantageously can be provided to the physician in a substantially dehydrated form (about 10% by weight of moisture, based on the total weight of the shield) and hydrated immediately prior to use. The hydrated shield, containing about 80% by weight of water, is applied to the eye and dissolves at a controlled rate under the prevailing physiological conditions of the eye, leaving substantially no residue.

The term "bio-erodible" as used herein means that the properly hydrated ophthalmic shield, under the physiological conditions present in the eye, slowly dissolves, eventually leaving no residue in the eye, typically over a period of from several hours to several days. The bio-erodibility characteristics of the shield can be adjusted by varying the degree of cross-linking of the shield and/or varying the amounts of gelatin, glycosaminoglycan and carboxymethyl cellulose present in the shield. Based upon the teachings herein, those skilled in this field will be able to prepare the presently-described and claimed ophthalmic shields having a desired dissolution rate.

Medical grade gelatin is commercially available from a variety of sources, or can be prepared by methods described in the literature. The gelatin employed in practicing this invention includes both Type A, derived from an acid-treated precursor, or Type B, derived from an alkali-treated precursor. Gelatin used to practice this invention can be obtained by partial hydrolysis of collagen derived from the skin, white connective tissues or bones of animals.

Gelatin is advantageously employed in concentrations ranging from about 50 to about 90 percent by weight, based upon the total weight of solids in the final product. Preferred concentrations are in the range from about 75 to about 80 percent.

Glycosaminoglycans are well-known biopolymers, generally characterized and described in the literature as copolymers of alternating hexose and aldouronic acid residues. These biopolymers, also commonly referred to as mucopolysaccharides, are found in connective tissue as the glycosylating polysaccharide chains of proteoglycans. Glycosaminoglycans frequently are present in their sulfated forms when not associated with a proteoglycan molecule. Examples of glycosaminoglycans include chondroitin sulfate, dermarin sulfate, keratin sulfate, dermatan sulfate, keratan sulfate, heparin sulfate, heparan sulfate and hyaluronic acid. Chondroitin sulfate is a preferred glycosaminoglycan that is well known, described in the literature and commercially available.

Chondroitin sulfate will be broken down by the complement of enzymes present in the normal eye, leading to acceptable dissolution properties of the ophthalmic shield. A primary function of the chondroitin sulfate will be to protect the ocular tissues against further trauma by inactivating enzymes that can harm the tissues, such as metalloproteases including collagenases, gelatinases, plasmin. Moreover, the presence of chondroitin sulfate may aid the re-epithelialization of the traumatized eye. Chondroitin sulfate is advantageously employed in concentrations ranging from about 2 to about 36 percent by weight, based on the total weight of solids in the final product. A preferred concentration is in the range of from about 8 to about 15 percent by weight.

Carboxymethyl cellulose also is commercially available in medical grade, typically as sodium carboxymethyl cellulose. This biopolymer is water soluble and, once the surrounding crosslinked matrix is broken down, will be absorbed by the surrounding tissue. Thus, this material, too, contributes to the desired dissolution properties of the ophthalmic shield and its versatility for use in the dry, traumatized or non-traumatized eye. Carboxymethyl cellulose is advantageously employed in preferred embodiments as its sodium salt in concentrations greater than 1% by weight, and up to 40% or even more, based on the total weight of solids in the final product. Preferably, the carboxymethyl cellulose will be present in an amount within the range of from about 5 to about 15 percent by weight.

While not wishing to be bound by any specific scientific theory, it is thought that the chondroitin sulfate and carboxymethyl cellulose biopolymers present in the ophthalmic shields of the invention function, in part, to sequester several of the metal cations (for example Fe and Ca cations) that are needed by, and function as cofactors for, a number of the metalloproteases that are present in elevated levels in the traumatized eye. This sequestering of the necessary cation cofactors inhibits the activity of the proteases and avoids the unacceptably fast dissolution of the ophthalmic shield—a problem encountered with some collagen-based shields when applied to traumatized eyes. Additionally, the chondroitin sulfate and carboxymethyl cellulose biopolymers assist in the healing of the traumatized eye by competing for the metal cations and thus deactivating the metallo-enzymes normally released at the site of trauma to the eye, which enzymes can attack healthy tissues if not inactivated. Thus, administration of the shield can reduce the damage that would otherwise be caused by proteolytic enzymes and thereby speed healing of an injured eye.

Other materials, such as fillers, can be included in the gelatin-based ophthalmic shields of the present invention. Examples of such fillers include, but are not limited to, polysaccharides such as the natural and modified agars, chitin, alginates and hydroxypropyl methylcellulose (HPMC), as well as polyvinyl alcohol. Such fillers can be incorporated in any amount which does not adversely affect the desired optical clarity, biocompatibility or bio-erodibility characteristics of the ophthalmic shield. Again, those skilled in this field will ascertain appropriate amounts of such materials based upon the desired physical characteristics of the final product.

It can be desirable to additionally incorporate an effective amount of an anti-oxidant into the formulation of the gelatin-based corneal shield, as both chondroitin sulfate and gelatin can be susceptible to oxidative breakdown. Antioxidants also will be useful for protecting the matrix from free radicals generated during gamma irradiation (sterilization) of the final product. Antioxidants suitable for use in ocular preparations are per se known by and available to those skilled in this field. Ascorbic acid is a preferred antioxidant for use in the formulations presented herein. About 1% by weight of ascorbic acid, based on the total weight of solids in the final product, is preferred.

The gelatin-based corneal shields of the present invention advantageously will be packaged for shipment in a "dry" state, wherein the total moisture content is about 10 to 15 percent by weight, based on the total weight of the shield. The shield contains hygroscopic materials, and reduction of the moisture content below 10 percent by weight typically requires an extra, and usually unnecessary, manufacturing step. The shields will be fully hydrated prior to use by, for example, soaking in a physiological saline solution, a BSS (balanced salts solution), or in any of a number of commercially-available ocular solutions. The fully hydrated shield will comprise about 80% by weight of water.

Soaking the shield in Optisol® brand corneal storage medium solution (a product of Chiron Vision Corporation, Irvine, Calif., USA; see U.S. Pat. No. 5,104,787, Apr. 14, 1992, Lindstrom et al., the entire disclosure of which is incorporated by reference herein) is one preferred method of rehydrating the inventive corneal shields. This rehydration method (and the resulting hydrated shield) can be used, for example, to promote healing following excimer laser keratectomy.

Optionally, a therapeutically active substance can be incorporated into the gelatin-based shield. The desired therapeutically active substance can be present in the rehydration solution, whereupon the substance will be incorporated into the shield during rehydration and will be slowly released to the eye as the shield dissolves. Alternatively, a therapeutically active substance can be present in, for example, the gelatin solution used to manufacture the shield. Substances that may be incorporated into the gelatin-based shield include, but are not limited to, those drugs generally used topically in ophthalmic indications, such as antivirals, antibiotics, steroidal and non-steroidal antiinflammatory agents, mydriatics, growth factors, anesthetics, analgesics and the like. For example, pilocarpine, tobramycin, gentamicin, dexamethasone, flurbiprofen, lidocaine and diclofenac can be incorporated into the gelatin-based shield of the present invention.

One possible use of the gelatin-based ophthalmic shield of the present invention is the treatment of traumatized or dry eyes of human patients. Application of the ophthalmic shield following excimer laser keratectomy surgery, or for treatment of dry eye, are particularly preferred applications of the inventive gelatin shield. In addition to the benefits discussed above, the shields provide, for example, comfort for post-surgical, post-traumatic and non-traumatic ocular conditions by providing a barrier film that temporarily separates the compromised ocular surface from eyelid movements. The dissolution of the shield provides a lubricating layer while normal healing occurs.

Methods for the manufacture of ophthalmic shields have been described in the literature, and the presently-described shields can be manufactured via such known procedures. For example, a sterile solution (in water for injection) of gelatin, sodium carboxymethyl cellulose, ascorbic acid (sodium salt) and chondroitin sulfate can be prepared. The solution (at a desired total solids concentration) is placed into contact lens molds and dried in an environment where temperature and humidity are controlled, for example at about 15°–30° C. and about 20–80% relative humidity. The resulting solid shields then are crosslinked by any of a number of per se known crosslinking methods. The shields can be crosslinked by, for example, chemical, UV light or vacuum-heat crosslinking methods. Following the desired extent of crosslinking, the shields are removed from the molds and packaged. Sterilization of the packaged product, for example via gamma radiation, is desirable.

The invention is illustrated by the following example:

EXAMPLE

A first solution is prepared containing high bloom bone gelatin, sodium carboxymethyl cellulose and ascorbic acid (from the sodium salt) in water for injection. A second water for injection solution of chondroitin sulfate is prepared, and the two solutions are combined to yield a solution having a total solids concentration of 2%, and such that on drying the solution yields a gelatin concentration of 79%, sodium carboxymethyl cellulose 10%, ascorbic acid sodium salt 1% and chondroitin sulfate 10%. The combined solutions are then sterilized by passage through a 0.2 μ filter.

The sterile solution is placed into contact lens molds having a base curve of 9.0 mm and a diameter of 14.5 mm. The solution is allowed to dehydrate in a vibration-free environment under controlled temperature (22°±1° C.) and humidity (40–45%) conditions. After approximately 48 hours, the total moisture content of the shields has reduced to about 15% by weight, whereupon the shields, still in the molds, are subjected to a vacuum-heat crosslinking procedure. Crosslinking is carried out under an inert ($N_2$) atmosphere at less than 1 mm of mercury and at a temperature between about 105 and 125° C. Crosslinking for 6–8 hours produces a shield that, when hydrated and placed in the eye of a patient, dissolves within approximately 12 to 14 hours.

The shields, in the form of a contact lens-shaped thin membrane, are removed from the molds and packaged. Sealed packages are sterilized via gamma radiation. The resulting shields exhibit excellent physical properties.

Those skilled in the art, based upon the foregoing discussion, will recognize that variations to both the formulation and the processing conditions can be made without departing from the scope of the appended claims. The amounts of glycosaminoglycan and carboxymethyl cellulose can be selected, as can the crosslinking method and time, so as to provide a shield having the desired dissolution and other physical properties.

I claim:

1. A bio-erodible ophthalmic shield, comprising a crosslinked matrix comprised of gelatin, a glycosaminoglycan and carboxymethyl cellulose.

2. A bio-erodible ophthalmic shield of claim 1, wherein the gelatin is present in a concentration ranging from about 50 to about 90 percent by weight.

3. A bio-erodible ophthalmic shield of claim 2 wherein the gelatin is present in a concentration of about 75 to about 80% by weight.

4. A bio-erodible ophthalmic shield of claim 1, wherein the glycosaminoglycan is chondroitin sulfate and is present in a concentration ranging from about 2 to about 36% by weight.

5. A bio-erodible ophthalmic shield of claim 4, wherein the chondroitin sulfate is present in a concentration of about 8 to about 15% by weight.

6. A bio-erodible ophthalmic shield of claim 1, further comprising an antioxidant.

7. A bio-erodible ophthalmic shield of claim 6, wherein the antioxidant is ascorbic acid.

8. A bio-erodible ophthalmic shield of claim 4, wherein the carboxymethyl cellulose is present in a concentration of about 5 to about 15 percent by weight.

9. A bio-erodible ophthalmic shield of claim 1, further comprising a therapeutically-effective amount of a therapeutically active substance.

10. A bio-erodible ophthalmic shield of claim 9 wherein the therapeutically active substance is a member selected from the group consisting of antiviral agents, antibiotic agents, steroidal and non-steroidal antiinflammatory agents, mydriatic agents, growth factors, anesthetic agents and analgesic agents.

11. A bio-erodible ophthalmic shield comprising a crosslinked matrix comprised of about 50–90% by weight of gelatin, 2–36% by weight of chondroitin sulfate and at least about 1% by weight of carboxymethyl cellulose.

12. A method of treating a traumatized eye of a patient, comprising applying to the traumatized eye a bio-erodible ophthalmic shield comprising a crosslinked matrix comprised of gelatin, glycosaminoglycan and carboxymethyl cellulose.

13. A method of claim 12, wherein the ophthalmic shield comprises a crosslinked matrix comprised of about 50–90% by weight of gelatin, 2–36% by weight of chondroitin sulfate and at least about 1% by weight of carboxymethyl cellulose.

14. A method of claim 12, wherein the ophthalmic shield further comprises, for those in need thereof, therapeutically-effective amount of a therapeutically active substance selected from the group consisting of antiviral agents, antibiotic agents, steroidal and nonsteroid antiinflammatory agents, mydriatic agents, growth factors, anesthetic agents and analgesic agents.

15. A method of reducing proteolytic damage to a traumatized eye, comprising applying to the traumatized eye a bio-erodible ophthalmic shield that is comprised of a crosslinked matrix comprising about 50–90% by weight of gelatin, 2–36% by weight of chondroitin sulfate and at least about 1% by weight of carboxymethyl cellulose.

16. A method of promoting wound healing following excimer laser keratectomy, comprising administering to an eye of a patient that has undergone an excimer laser keratectomy procedure a bio-erodible ophthalmic shield that comprises a crosslinked matrix comprised of gelatin, glycosaminoglycan and carboxymethyl cellulose.

17. A method according to claim 12, wherein the crosslinked matrix comprises about 50–90% by weight of gelatin, 2–36% by weight of chondroitin sulfate and at least about 1% by weight of carboxymethyl cellulose.

18. A bio-erodible ophthalmic shield prepared by crosslinking a dehydrated solution comprising gelatin, a glycosaminoglycan and carboxymethyl cellulose.

19. An ophthalmic shield according to claim 18, wherein the glycosaminoglycan is chondroitin sulfate.

* * * * *